United States Patent
Wu et al.

(10) Patent No.: US 6,730,806 B2
(45) Date of Patent: May 4, 2004

(54) PROCESS FOR PREPARING A CARBOXYLIC ESTER

(75) Inventors: Kuo-Ching Wu, Hsinchu (TW); Wen-Tzong Liu, Hsinchu (TW); Rey-Yue Chang, Hsinchu Hsien (TW); Chin-Shu Tsai, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 10/190,544

(22) Filed: Jul. 9, 2002

(65) Prior Publication Data

US 2003/0109742 A1 Jun. 12, 2003

(30) Foreign Application Priority Data

Dec. 5, 2001 (TW) ........................................ 90130084 A

(51) Int. Cl.7 .............................................. C07C 67/02
(52) U.S. Cl. ........................................ 560/254; 560/265
(58) Field of Search ................................ 560/254, 265, 560/103, 105, 106, 231

(56) References Cited

U.S. PATENT DOCUMENTS 5,719,311 A * 2/1998 Wu et al. ..................... 560/98

FOREIGN PATENT DOCUMENTS

| DE | 2 148 719 | * | 6/1972 |
| FR | 2005278 | * | 12/1969 |
| GB | 1 333 008 | * | 10/1973 |
| WO | WO 99/48855 | * | 9/1999 |

* cited by examiner

Primary Examiner—Richard L. Raymond
Assistant Examiner—Zachary C. Tucker
(74) Attorney, Agent, or Firm—Sughrue Mion, PLLC

(57) ABSTRACT

A process for preparing carboxylic esters. A catalytic distillation column filled with acidic catalyst in solid phase is utilized. Alcohol is fed from the bottom of the catalytic distillation column, and carboxylic acid or carboxylic anhydride is fed from the top of the catalytic distillation column in such a manner that the carboxylic acid or carboxylic anhydride can remain in the catalytic distillation column for a sufficient time to cause the esterification to produce the carboxylic ester and water. An esterification pre-reactor can be connected in series with the catalytic distillation column to facilitate the esterification.

12 Claims, No Drawings

PROCESS FOR PREPARING A CARBOXYLIC ESTER

BACKGROUND OF THE INVENTION

1. Field of the Invention

The present invention relates to a process for preparing a carboxylic ester. In particular, the present invention relates to a catalytic distillation process utilizing acidic catalysts in solid phase for the preparation of carboxylic esters. This catalytic distillation process is especially suitable for the preparation of carboxylic ester having a relative volatility with the reactant: carboxylic acid, close to 1.

2. Background of the Invention

U.S. Pat. No. 5,719,311, the content thereof is incorporated herein by reference, discloses a fixed bed catalytic process for the esterification of carboxylic acids and alcohol into carboxylic esters. In the process disclosed in the '311 patent, the fixed bed reactor contains acidic catalysts that are present in solid phase, and the reaction condition is controlled such that (i) the reactants and the products co-exist in a gas-liquid two-phase equilibrium in the fixed bed reactor and that (ii) at least one component of the reactants is present in one phase and at least one component of the products is present in another phase. Very high reaction yield and selectivity, typically better than 90%, sometimes exceeding 99%, were observed with the process disclosed in the '311 patent for preparing the esters of methanol/propionic acid, methanol/methacrylic acid, isobutanol/hexahydrophthalic anhydride, and isooctyl alcohol/phthalic anhydride. However, when the carboxylic acid is acetic acid, which has high miscibility with many alcohols, the reaction yield from the process of the '311 patent will not be the same high level as with other carboxylic acids, and conventional processes need to be used to produce esters of acetic acid in an economic manner. Lowered reaction yield causes unsatisfactory amounts of alcohol to remain in the production, thus further adversely affecting the economic potential of the process, especially with regard to post-esterification purification cost.

To solve the problem encountered with the preparation of acetic esters, U.S. Pat. No. 5,998,659 proposes a catalytic process for the preparation of acetic esters. According to the proposed process, a fixed bed catalytic esterification and a catalytic distillation are utilized. This catalytic process is able to achieve excellent esterification yield of acetic acid and provide post esterification with substantially reduced height of the distillation column. However, this process is not suitable for the preparation of carboxylic esters that has a relative volatility with the reactant, carboxylic acid, close to 1, because carboxylic esters with high boiling point are not suitable for discharge from the top of the catalytic distillation column. Collection of esterification products from the top of the catalytic distillation column necessitates a large amount of refluxed water, making the process impractical and uneconomical.

SUMMARY OF THE INVENTION

It is therefore an object of the invention to provide an improved process for preparing carboxylic esters having high boiling point from carboxylic acids and alcohols.

It is another object of the invention to provide a process for preparing carboxylic esters, which is able to achieve excellent esterification yield, sometimes exceeding 99.8% and thus reduce the post-esterification separation and production costs.

To attain the objects mentioned above, the process of the invention utilizes a catalytic distillation column containing acidic catalyst in solid phase. In accordance with the present invention, the esterification reaction can be accomplished in this catalytic distillation column, or the catalytic distillation column can be connected to the downstream of an esterification reactor. The catalytic distillation column is so designed that when no esterification pre-reactor is used, the alcohol is fed from the bottom portion thereof, and the carboxylic acid is fed from the top portion. When a pre-reactor is used, the alcohol is fed from the bottom portion of the distillation column, and the reaction product from the pre-reactor is fed from the top portion thereof. In other words, the esterification and extraction of the esterification product are conducted in a counter-flow manner. Note that the residence time of the carboxylic acids in the catalytic distillation column must be sufficient to accomplish high reactant conversion and to produce carboxylic esters and water. Also, note that according to the process of the invention, the alcohol and water are continuously removed from the top of the catalytic distillation column, and the carboxylic esters are continuously removed from the bottom.

By using the catalytic distillation process, the distillate from the bottom contains more than 99.8% of the carboxylic esters. Because of the high esterification yield, the post-esterification purification can be simplified and the amount of energy consumption can also be greatly reduced. Also, a mixed solution discharged from the top of the catalytic distillation column is then separated by a separator, for example a decanter, into water phase and organic phase. The organic phase, comprising alcohols, carboxylic esters and carboxylic acids, is directly refluxed into the catalytic distillation column and the water phase is stripped to recycle residual organic composition. By using the catalytic process of the invention, the amount of energy consumption can be greatly reduced to ⅔ of a conventional catalytic process, and in practical application 1–2 purification distillation columns can be saved.

DETAILED DESCRIPTION OF THE INVENTION

The carboxylic acids of the esterification reactants, which may be suitable for use in this invention, are straight-chain, branched, and aromatic carboxylic acids having a carbon number from 2 to 10. An anhydride of the above-mentioned carboxylic acids is also suitable for the purpose of the invention. The catalytic process of the invention is especially suitable for the esterificatin of propionic acid and acetic acids which are the esterification reactants of commercially available propionic esters and acetic esters.

Other esterification reactants, alcohols can be straight-chain, branched and aromatic alcohols having a carbon number from 1–12. Note that according to an aspect of the invention, the carboxylic esters and alcohols must be so selected that the resulting carboxylic esters have the highest boiling point in the whole reaction system and have a boiling point higher than 100° C.

The catalytic distillation column utilized according to the invention can be one which includes several sections disposed vertically, each section respectively filled with packing material or solid acid catalysts. For example, a catalytic distillation column, including, from the bottom to the top, stripping section, reaction section, extractive distillation section, and rectification section, is preferred. The stripping section and rectification section can be filled with packing materials, such as PRO-PAK packing material available from Sulzer. The reaction section and the extractive distillation section are filled with solid acidic catalysts. The solid acidic catalysts suitable for use in this invention include but are not limited to oxide, zeolite, cation-exchange resins or a mixture thereof. Among them, $SO_4^{2-}/ZrO_2$ oxide, or HZSM-5 zeolite, is preferred.

As mentioned in the summary section, the catalytic distillation column can be connected in series with a esterification pre-reactor. Preferably, the pre-reactor is a fixed bed reactor inside which is packed with solid acid catalyst. Also, preferably, the fixed bed reactor is controlled under a reaction condition that reactants and reaction products co-exist in a gas-liquid two-phase equilibrium and that at least one component of the reactants is present in one phase and at least one component of the reaction products is present in another phase. For example, in the preparation of N-butyl propionate, in the fixed bed reactor, the propionic acid is in liquid phase and is charged into the upper portion of the fixed bed reactor together with alcohol in gas phase, while the resulting N-butyl propionate and water are discharged from the bottom portion thereof in gas phase.

Without any intent to limit the scope of this invention, the present invention will be hereinafter explained in more detail with reference to the examples. Note that in the following examples, the reaction yield of the carboxylic ester is defined as below.

$$\text{Yield} = \frac{\text{moles of carboxylic ester in the product}}{\text{moles of alcohol in the feed}}$$

EXAMPLE 1

A 50 mm stainless tube was used as a catalytic distillation column in this example. The top portion and the bottom portion were packed with PRO-PAK packing materials to act as rectification section and stripping section respectively. The HETP of the rectification section and the stripping section was set as 12 and 10 respectively. The middle portion of the stainless tube was filled with 410 grams of Amberlite 36 catalyst (from Rohm Hass Co. Ltd.) to act as reaction and extraction section. The packing density of the catalyst is about 200 g/l. This distillation column is equipped with a decanter at the top thereof, an upper feeding plate located at the top of the reaction section, and lower feeding plate located at the bottom of the reaction section. Propionic acid was fed into the catalytic distillation column from the upper feeding plate at a flow rate of 4.5 g/min and n-butanoic acid was fed into the catalytic distillation column from the lower feeding plate at a flow rate of 15.0 g/min. The organic phase collected by the decanter was refluxed to the catalytic distillation column at a reflux/distillate ratio of 1.8–2.2. The esterification product, the n-butyl propionate solution, was discharged from the bottom of the distillation column. After cooling, the esterification product and the distillate obtained from the top of the distillation column were analyzed using gas chromatography, and the results are indicated in Table 1 below.

TABLE 1

| position at the catalytic distillation column | n-butanol feed | Propionic acid feed | bottom discharge | top discharge (before decanter) |
|---|---|---|---|---|
| flow rate (g/min) | 15.0 | 4.5 | 7.5 | 3.5 |
| composition (wt %) | | | | |
| propionic acid | — | >99.8% | 0.16% | — |
| n-butanol | >99.8% | — | — | 84.58% |
| n-butyl propionate | — | — | 99.84% | 2.06% |
| water | — | — | — | 13.36% |

Note: The gas chromatograph can only analysissay a substance having a concentration greater than 0.01 wt %.

Table 1 shows that the content of the propionic acid in the bottom charge and top charge stream is below 2.0 wt %, and the reaction yield of the n-butyl propionate in the bottom discharge stream is higher than 99.84%. This is indicative that the catalytic process of the invention can achieve excellent estierification yield and reduce the post esterification purification process.

EXAMPLE 2

A fixed-bed reactor as described in U.S. Pat. No. 5,719,311 and the catalytic distillation column used in example 1 were used in this example. A reaction composition containing n-butanol and propionic acid at an n-butanol/propionic acid ratio of 1.5 was fed into the fixed reactor from the upper portion of the fixed bed reactor. The reaction product from the fixed bed reactor was fed from the upper feeding plate into the catalytic distillation column at a flow rate of 19.2 g/min, and concurrently fresh n-butanol was fed from the lower feeding plate into the catalytic distillation column at a flow rate of 4.2 g/min. The organic phase obtained from the decanter was refluxed into the distillation column at a reflux/discharge rate of 1.4–1.6. The esterification product, the n-butyl propionate solution was discharged from the bottom of the distillation column. After cooling, the esterification product and the distillate obtained from the top of the distillation column were analyzed using gas chromatography, and the results are indicated in Table 2 below.

TABLE 2

| position at the catalytic distillation column | n-butanol feed | propionic acid feed | bottom discharge | top discharge (before decanter) |
|---|---|---|---|---|
| flow rate (g/min) | 4.2 | 19.2 | 12.7 | 27 |
| composition (wt %) | | | | |
| propionic acid | — | 2.508 | — | — |
| n-butanol | >99.8% | 19.56% | — | 71.17% |
| n-butyl propionate | — | 67.39% | 100.00% | 2.00% |
| water | — | 10.55% | — | 26.83% |

Table 2 shows that the content of the propionic acid in the bottom charge and top charge stream is below 100 ppm, and the reaction yield of the n-butyl propionate in the bottom discharge stream closes to 100%. This is indicative that using an esterification pre-reactor can increase the capacity of the catalytic distillation column and produce carboxylic esters at a much higher yield.

EXAMPLE 3

The same catalytic distillation column as in example 1 was used in this example. However, the HETP of the rectification section and the stripping section was set as 20 and 10 respectively, and 400 grams of Amberlite 36 catalyst (from Rohm Hass Co. Ltd.) was packed in the middle portion to act as reaction and extraction section. A fixed-bed reactor as described in U.S. Pat. No. 5,719,311 was also used in series with the catalytic distillation column. A reaction composition containing n-butanol and acetic acid at an n-butanol/acetic acid ratio of 1.5 was fed into the fixed reactor from the upper portion of the fixed bed reactor. The reaction product from the fixed bed reactor was fed from the upper feeding plate into the catalytic distillation column at a flow rate of 15.6 g/min, and concurrently fresh n-butanol was fed from the lower feeding plate into the catalytic distillation column at a flow rate of 4.9 g/min. The organic phase obtained from the decanter was refluxed into the distillation column at a reflux/discharge rate of 1.8–2.2. The esterification product, the n-butyl acetate solution was discharged from the bottom of the distillation column. After cooling, the esterification product and the distillate obtained from the top of the distillation column were analyzed using gas chromatography, and the results are indicated in Table 3 below.

TABLE 3

| position at the catalytic distillation column | n-butanol feed | acetic acid feed | bottom discharge | top discharge (before decanter) |
|---|---|---|---|---|
| flow rate (g/min) | 4.9 | 15.6 | 10.1 | 31 |
| composition (wt %) | | | | |
| acetic acid | — | 1.40% | — | — |
| n-butanol | >99.8% | 23.35% | — | 86.77% |
| n-butyl acetate | — | 65.14% | 100.00% | 2.33% |
| water | — | 10.11% | — | 10.90% |

Table 3 shows that the content of the acetic acid in the bottom charge and top charge stream is below 100 ppm, and the reaction yield of the n-butyl acetate in the bottom discharge stream closes to 100%. This is indicative that the catalytic process of the invention can achieve excellent estierification yield and reduce the post esterification purification process.

What is claimed is:

1. A process for preparing a carboxylic ester from esterification reactants comprising a carboxylic acid or a carboxylic anhydride and at least one alcohol, wherein the carboxylic acid is propionic acid, wherein the carboxylic ester has a boiling point higher than the boiling point of the carboxylic acid or the carboxylic anhydride and the alcohol and higher than 100° C.; the process comprising the following steps:

(a) charging the alcohol from the bottom of a catalytic distillation column containing at least one acidic catalyst in a solid phase, and charging the carboxylic acid or carboxylic anhydride from the top of the catalytic distillation column in such a manner that the carboxylic acid or carboxylic anhydride can remain in the catalytic distillation column for a sufficient time to cause the esterification to produce the carboxylic ester and water, and the alcohol to flow upward and the reaction product to flow downward in a counter-flow manner; and (b) continuously removing the alcohol and water from the top of the catalytic distillation column, and continuously removing the carboxylic esters from the bottom of the catalytic distillation column.

2. The process as claimed in claim 1, wherein the alcohol is an alcohol selected from the group consisting of a straight-chain, branched, and aromatic alcohol having a carbon number from 1 to 12.

3. The process as claimed in claim 2, wherein the alcohol is n-butanol.

4. The process as claimed in claim 1, wherein the acid catalyst is a catalyst selected from the group consisting of oxide, zeolite, cation-exchange resin and a mixture thereof.

5. The process as claimed in claim 4, wherein the acid catalyst is $SO_4^{2-}/ZrO_2$ oxide.

6. A process for preparing a carboxylic ester from esterification reactants comprising a carboxylic acid or a carboxylic anhydride and at least one alcohol, wherein the carboxylic acid is acetic acid or propionic acid, wherein the carboxylic ester has a boiling point higher than the boiling point of the carboxylic acid or the carboxylic anhydride and the alcohol and higher than 100° C.; the process comprising:

subjecting the reactants to an esterification in a fixed bed catalytic reactor wherein the esterification comprises reacting the reactants in a fixed bed including acidic catalyst in a solid phase to form reaction products comprising the carboxylic ester, water, and residual carboxylic acid, under a reaction condition that the reactants and the reaction products co-exist in a gas-liquid two-phase equilibrium in the fixed bed and that at least one component of the reactants is present in one phase and at least one component of the reaction products is present in another phase, followed by a catalytic distillation comprising the following steps:

(a) charging a fresh alcohol from the bottom of a catalytic distillation column containing at least one acidic catalyst in a solid phase, and charging the reaction products from the fixed bed catalytic reactor from the top of the catalytic distillation column in such a manner that the residual carboxylic acid can remain in the catalytic distillation column for a sufficient time to cause further esterification, and the alcohol to flow upward and the reaction product to flow downward in a counter-flow manner; and (b) continuously removing the alcohol and water from the top of the catalytic distillation column, and continuously removing the carboxylic esters from the bottom of the catalytic distillation column.

7. The process as claimed in claim 6, wherein the carboxylic acid is propionic acid.

8. The process as claimed in claim 6, wherein the carboxylic acid is acetic acid.

9. The process as claimed in claim 6, wherein the alcohol is an alcohol selected from the group consisting of straight-chain, branched, and aromatic alcohol having a carbon number from 1 to 12.

10. The process as claimed in claim 9, wherein the alcohol is n-butanol.

11. The process as claimed in claim 6, wherein the acid catalyst is a catalyst selected from the group consisting of oxide, zeolite, cation-exchange resin, and a mixture thereof.

12. The process as claimed in claim 6, wherein the acid catalyst is $SO_4^{2-}/ZrO_2$ oxide.

* * * * *